United States Patent
Elachchabi et al.

(10) Patent No.: US 10,206,769 B2
(45) Date of Patent: Feb. 19, 2019

(54) IMPLANTABLE DEVICES INCLUDING A FILM PROVIDING FOLDING CHARACTERISTICS

(71) Applicant: Covidien LP, Mansfield, MA (US)

(72) Inventors: Amin Elachchabi, Hamden, CT (US); Joshua Stopek, St. Louis Park, MN (US); Daniel Broom, Branford, CT (US)

(73) Assignee: COVIDIEN LP, Mansfield, MA (US)

( * ) Notice: Subject to any disclaimer, the term of this patent is extended or adjusted under 35 U.S.C. 154(b) by 129 days.

(21) Appl. No.: 13/780,113

(22) Filed: Feb. 28, 2013

(65) Prior Publication Data

US 2013/0261542 A1  Oct. 3, 2013

Related U.S. Application Data

(60) Provisional application No. 61/617,827, filed on Mar. 30, 2012.

(51) Int. Cl.
*A61F 2/00*     (2006.01)

(52) U.S. Cl.
CPC .... *A61F 2/0063* (2013.01); *A61F 2002/0068* (2013.01); *A61F 2250/0029* (2013.01); *A61F 2250/0036* (2013.01)

(58) Field of Classification Search
CPC ............ A61F 2/0063; A61F 2002/0068; A61F 2210/0076; A61F 2250/0036; A61F 2250/0029
USPC ................. 623/23.72, 23.74; 606/151, 213
See application file for complete search history.

(56) References Cited

U.S. PATENT DOCUMENTS

| | | |
|---|---|---|
| 3,054,406 A | 9/1962 | Usher |
| 3,276,448 A | 10/1966 | Kronenthal |
| 3,851,034 A | 11/1974 | Harmon et al. |
| 3,887,699 A | 6/1975 | Yolles |
| 4,767,628 A | 8/1988 | Hutchinson |
| 4,931,546 A | 6/1990 | Tardy et al. |
| 5,116,357 A | 5/1992 | Eberbach |
| 5,147,374 A | 9/1992 | Fernandez |
| 5,195,542 A | 3/1993 | Gazielly et al. |
| 5,201,745 A | 4/1993 | Tayot et al. |
| 5,254,133 A | 10/1993 | Seid |
| 5,258,000 A | 11/1993 | Gianturco |
| 5,368,602 A | 11/1994 | de la Torre |
| 5,370,650 A | 12/1994 | Tovey et al. |
| 5,397,331 A | 3/1995 | Himpen |
| 5,593,441 A | 1/1997 | Lichtenstein et al. |

(Continued)

FOREIGN PATENT DOCUMENTS

| | | |
|---|---|---|
| DE | 10 2008 059245 A1 | 5/2010 |
| EP | 1 674 048 A1 | 6/2006 |

(Continued)

OTHER PUBLICATIONS

European Search Report for Application No. 13 15 5349 dated Apr. 4, 2013 (6 pages).

(Continued)

*Primary Examiner* — Anh T Dang (57) ABSTRACT

The present disclosure relates to implantable medical devices which include a film which includes predetermined folding characteristics via predetermined thicknesses along different areas of the implant.

19 Claims, 7 Drawing Sheets

(56) References Cited

U.S. PATENT DOCUMENTS

| | | |
|---|---|---|
| 5,634,931 A | 6/1997 | Kugel |
| 5,676,967 A | 10/1997 | Williams et al. |
| 5,695,525 A | 12/1997 | Mulhauser et al. |
| 5,702,416 A | 12/1997 | Kieturakis et al. |
| 5,743,917 A | 4/1998 | Saxon |
| 5,766,246 A | 6/1998 | Mulhauser et al. |
| 5,769,864 A | 6/1998 | Kugel |
| 5,711,960 A | 7/1998 | Shikinami |
| 5,916,225 A | 6/1999 | Kugel |
| 5,919,232 A | 7/1999 | Chaffringeon et al. |
| 5,922,026 A | 7/1999 | Chin |
| 6,042,534 A | 3/2000 | Gellman et al. |
| 6,090,116 A | 7/2000 | D'Aversa et al. |
| 6,113,623 A | 9/2000 | Sgro |
| 6,120,539 A | 9/2000 | Eldridge et al. |
| 6,162,962 A | 12/2000 | Hinsch et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,180,848 B1 | 1/2001 | Flament et al. |
| 6,197,935 B1 | 3/2001 | Doillon et al. |
| 6,201,439 B1 | 4/2001 | Firmin et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,270,792 B1 | 8/2001 | Guillemet et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,319,264 B1 | 11/2001 | Tömälä |
| 6,383,201 B1 | 5/2002 | Dong |
| 6,398,814 B1 | 6/2002 | Paasimaa et al. |
| 6,425,924 B1 | 7/2002 | Rousseau |
| 6,447,551 B1 | 9/2002 | Goldmann |
| 6,485,503 B2 | 11/2002 | Jacobs et al. |
| 6,500,777 B1 | 12/2002 | Wiseman et al. |
| 6,596,002 B2 | 7/2003 | Therin et al. |
| 6,610,006 B1 | 8/2003 | Amid et al. |
| 6,616,685 B2 | 9/2003 | Rousseau |
| 6,645,226 B1 | 11/2003 | Jacobs et al. |
| 6,652,595 B1 * | 11/2003 | Nicolo .................... 623/23.74 |
| 6,669,735 B1 | 12/2003 | Pelissier |
| 6,712,859 B2 | 3/2004 | Rousseau et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,746,458 B1 | 6/2004 | Cloud |
| 6,755,868 B2 | 6/2004 | Rousseau |
| 6,790,213 B2 | 9/2004 | Cherok et al. |
| 6,800,082 B2 | 10/2004 | Rousseau |
| 6,872,227 B2 | 3/2005 | Sump et al. |
| 6,926,723 B1 | 8/2005 | Mulhauser et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,041,868 B2 | 5/2006 | Greene et al. |
| 7,060,103 B2 | 6/2006 | Carr, Jr. et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,101,381 B2 | 9/2006 | Ford et al. |
| 7,156,804 B2 | 1/2007 | Nicolo |
| 7,156,858 B2 | 1/2007 | Schuldt-Hempe et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,404,199 B2 | 7/2008 | Arneson et al. |
| 7,556,598 B2 | 7/2009 | Rao |
| 7,594,921 B2 | 9/2009 | Browning |
| 7,614,258 B2 | 11/2009 | Cherok et al. |
| 7,641,958 B2 * | 1/2010 | Berman et al. ............. 428/143 |
| 7,732,354 B2 | 6/2010 | Fricke et al. |
| 7,785,334 B2 | 8/2010 | Ford et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 8,100,924 B2 | 1/2012 | Browning |
| 8,123,817 B2 | 2/2012 | Intoccia et al. |
| 8,157,821 B2 | 4/2012 | Browning |
| 8,157,822 B2 | 4/2012 | Browning |
| 8,182,545 B2 | 5/2012 | Cherok et al. |
| 8,206,632 B2 | 6/2012 | Rousseau et al. |
| 8,215,310 B2 | 7/2012 | Browning |
| 2001/0056303 A1 | 12/2001 | Caneiro et al. |
| 2002/0099344 A1 | 7/2002 | Hessel et al. |
| 2002/0131988 A1 | 9/2002 | Foster et al. |
| 2003/0130745 A1 | 7/2003 | Cherok et al. |
| 2004/0098118 A1 | 5/2004 | Granada et al. |
| 2004/0215219 A1 | 10/2004 | Eldridge et al. |
| 2004/0224007 A1 | 11/2004 | Zhang |
| 2005/0113849 A1 | 5/2005 | Popadiuk et al. |
| 2005/0240261 A1 | 10/2005 | Rakos et al. |
| 2005/0244455 A1 | 11/2005 | Greenawalt |
| 2005/0261782 A1 | 11/2005 | Hoganson |
| 2006/0034887 A1 | 2/2006 | Pelissier |
| 2006/0116696 A1 | 6/2006 | Odermatt et al. |
| 2006/0121078 A1 | 6/2006 | Trogolo et al. |
| 2006/0188546 A1 | 8/2006 | Giroux |
| 2006/0224038 A1 | 10/2006 | Rao |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0244548 A1 | 10/2007 | Myers et al. |
| 2007/0260268 A1 | 11/2007 | Bartee et al. |
| 2007/0276477 A1 * | 11/2007 | Lee et al. ................ 623/1.44 |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0147200 A1 | 6/2008 | Rousseau et al. |
| 2008/0161837 A1 | 7/2008 | Toso et al. |
| 2008/0172071 A1 | 7/2008 | Barker |
| 2008/0199506 A1 | 8/2008 | Horres et al. |
| 2008/0255593 A1 | 10/2008 | St-Germain |
| 2009/0036996 A1 | 2/2009 | Roeber |
| 2009/0069826 A1 | 3/2009 | Walther et al. |
| 2009/0082792 A1 | 3/2009 | Koyfinan et al. |
| 2009/0105526 A1 | 4/2009 | Piroli Torelli et al. |
| 2009/0125107 A1 | 5/2009 | Maxwell |
| 2009/0142385 A1 | 6/2009 | Gross et al. |
| 2009/0152766 A1 * | 6/2009 | Rousseau ............. A61L 27/50<br>264/241 |
| 2009/0163936 A1 | 6/2009 | Yang et al. |
| 2009/0171377 A1 | 7/2009 | Intoccia et al. |
| 2009/0187197 A1 | 7/2009 | Roeber et al. |
| 2009/0192530 A1 | 7/2009 | Adzich et al. |
| 2009/0192532 A1 | 7/2009 | Spinnler et al. |
| 2009/0198260 A1 | 8/2009 | Ford et al. |
| 2009/0270999 A1 | 10/2009 | Brown |
| 2009/0276057 A1 | 11/2009 | Trabucco et al. |
| 2009/0299538 A1 | 12/2009 | Suzuki |
| 2009/0326676 A1 | 12/2009 | Dupic et al. |
| 2010/0003308 A1 | 1/2010 | Tapolsky et al. |
| 2010/0089409 A1 | 4/2010 | Bertagnoli |
| 2010/0160375 A1 | 6/2010 | King |
| 2010/0286716 A1 | 11/2010 | Ford et al. |
| 2010/0312043 A1 | 12/2010 | Goddard |
| 2010/0318108 A1 | 12/2010 | Datta et al. |
| 2011/0144667 A1 | 1/2011 | Horton et al. |
| 2011/0238094 A1 | 9/2011 | Thomas et al. |
| 2011/0257666 A1 | 10/2011 | Ladet et al. |
| 2011/0264120 A1 | 10/2011 | Bayon et al. |
| 2011/0265283 A1 | 11/2011 | Duncan |
| 2011/0293688 A1 | 12/2011 | Bennett et al. |
| 2012/0010637 A1 | 1/2012 | Stopek et al. |
| 2012/0016388 A1 | 1/2012 | Houard et al. |

(56) References Cited

U.S. PATENT DOCUMENTS

| | | |
|---|---|---|
| 2012/0029537 A1 | 2/2012 | Mortarino |
| 2012/0029540 A1 | 2/2012 | Adams |
| 2012/0053602 A1 | 3/2012 | Adzich et al. |
| 2012/0065727 A1 | 3/2012 | Reneker et al. |
| 2012/0082712 A1 | 4/2012 | Stopek et al. |
| 2012/0109165 A1 | 5/2012 | Mathisen et al. |
| 2012/0116423 A1 | 5/2012 | Gleiman et al. |
| 2012/0116425 A1 | 5/2012 | Intoccia et al. |
| 2012/0150204 A1 | 6/2012 | Mortarino et al. |
| 2012/0179175 A1 | 7/2012 | Hammell |
| 2012/0179176 A1 | 7/2012 | Wilson et al. |
| 2012/0239063 A1 | 9/2012 | Lee |
| 2012/0253472 A1* | 10/2012 | Priewe .................. A61L 27/14 623/23.72 |
| 2012/0259348 A1 | 10/2012 | Paul |
| 2013/0060263 A1 | 3/2013 | Bailly et al. |

FOREIGN PATENT DOCUMENTS

| | | |
|---|---|---|
| EP | 2 016 956 A2 | 1/2009 |
| EP | 2 404 571 A1 | 1/2012 |
| FR | 2 601 371 A1 | 1/1988 |
| FR | 2 857 851 A1 | 1/2005 |
| WO | WO 93/11805 A1 | 6/1993 |
| WO | WO 99/51163 A1 | 10/1999 |
| WO | WO 02/34304 A1 | 5/2002 |
| WO | WO 03/007847 A1 | 1/2003 |
| WO | WO 03/099160 A1 | 12/2003 |
| WO | WO 2006/020922 A2 | 2/2006 |
| WO | WO 2006/036967 A1 | 4/2006 |
| WO | WO 2006/102374 A2 | 9/2006 |
| WO | WO 2008/002815 A2 | 1/2008 |
| WO | WO 2008/127411 A1 | 10/2008 |
| WO | WO 2009/075786 A1 | 6/2009 |
| WO | WO 2010/093333 A1 | 8/2012 |

OTHER PUBLICATIONS

European Search Report corresponding to European Application No. EP 13 16 1532, completed on Jun. 14, 2013 dated Jun. 24, 2013; 7 pages.

* cited by examiner

IMPLANTABLE DEVICES INCLUDING A FILM PROVIDING FOLDING CHARACTERISTICS

CROSS-REFERENCE TO RELATED APPLICATIONS

This application claims the benefit of and priority to U.S. Provisional Patent Application No. 61/617,827, filed Mar. 30, 2012, the entire disclosure of which is incorporated by reference herein.

BACKGROUND

Technical Field

The present disclosure relates generally to implantable medical devices, and more particularly, to implantable medical devices which include at least one foldable film which includes predetermined folding characteristics.

Background of Related Art

Implantable medical devices may be used during both laparoscopic and open surgery for repair of many types of tissue defects and injuries. Some non-limiting examples of such devices include sutures, staples, mesh, films, and the like. Some non-limiting examples of such tissue defects or injuries include hernias, prolapses, fistulas, stomas, and the like.

During surgery, at least one small surgical incision may be made in the tissue to create access into the body. In some instances, the incision may be filled with a surgical device, such as catheter, cannula, trocar and the like, which maintains access into the body. In each instance, the opening in the tissue and/or the opening in the surgical device may not be large enough to allow for the passage of an implantable medical device in its normal configuration. For example, a surgical mesh may be configured to have a width or length which is larger than the diameter of the incision created in the skin to provide access to the herniated tissue. In such instances the mesh may be altered from its original configuration to a smaller configuration so that it may be sufficiently small to pass through the incision.

Upon passing through the smaller incisional opening in a smaller configuration, the implant may need to be returned to its original larger configuration before being properly secured in the tissue. Since, the site of implantation may be small, and in some instances access may be limited, returning the implant to its original larger configuration may be difficult and/or time consuming. Thus, it would be beneficial to provide an implant which includes a film having predetermined folding characteristics which can be easily folded and easily returns to its original unfolded configuration upon implantation.

SUMMARY

Accordingly, the present disclosure relates to implantable medical devices which include at least one foldable film which includes predetermined folding characteristics. The foldable films described herein may include at least a first area having a first thickness, and a second area having a second thickness different from the first thickness. The first thickness may be the same as or different than the third thickness. In embodiments, the films further include a third area having a third thickness, wherein the second area is positioned between the first and third areas of the film and the second thickness of the second area is less than the first thickness and the third thickness.

In embodiments, the implantable medical devices described herein may include a foldable film which includes a first area having a first thickness and a second area having a second thickness which is less than the first thickness of the first area, wherein the first and second areas alternate along the length of the device. In embodiments, the first and second areas extend along the outer edge of the device. It is envisioned that the films may be fold along the thinner second areas.

In embodiments, the implantable medical devices further include at least one reinforcement member. In addition, the devices described herein may optionally include a slit, aperture, and/or therapeutic agent.

In still other embodiments, the foldable films may be a single layer of different thicknesses. In yet other embodiments, the foldable films may include multiple polymeric layers.

Methods of forming such devices are also disclosed.

BRIEF DESCRIPTION OF THE DRAWINGS

The foregoing objects and advantages of the disclosure will become more apparent from the reading of the following description in connection with the accompanying drawings, in which.

DETAILED DESCRIPTION

The present disclosure relates to implantable medical devices which include a foldable film having predetermined folding characteristics. The films ability to fold may be determined by changes in thickness along the length of the device.

The foldable films include at least a first area having a first thickness, and a second area having a second thickness different from the first thickness. In embodiments, the films further include a third area having a third thickness, wherein the second area is positioned between the first and third areas of the film and the second thickness of the second area is less than the first thickness and the third thickness.

In embodiments, the films described herein may preferentially fold along the areas which are thinner than the other thicker areas of the implant. It is envisioned that by arranging the thickness of the film at various locations, the films described herein may be made to directionally or preferentially fold into a predetermined configuration. For example, in some embodiments, the films described herein may be folded into a stacked configuration (FIG. 1C) which may be useful for passing the folded implant through an opening in the tissue and/or an opening in a surgical device, such as a cannula, catheter, trocar and the like, wherein the opening in the tissue and/or device is smaller than the unfolded configuration of the implant.

Without intending to limit the present disclosure, the difference in thicknesses between the first and second areas of the film is sufficient to allow the implant to fold along the thinner areas of the film. In embodiments, the thickness of the first area and the thickness of the second area may be at a ratio ranging from about 1.5:1 to about 30:1, and in embodiments, from about 2:1 to about 20:1, and still in other embodiments from about 3:1 to about 10:1.

By implantable, the medical devices described herein may be positioned, for any duration of time, at a location within a body, such as within a portion of the abdominal cavity. Furthermore, the terms "implantation" and "implanted" refer to the positioning, for any duration of time, of a medical device at a location within a body, such as within a portion of the abdominal cavity.

The medical devices described herein include at least one foldable film which may be made from any biocompatible material. Suitable biocompatible materials include bioabsorbable and non-bioabsorbable materials, each of which may comprise synthetic or natural materials. Suitable materials are within the purview of those skilled in the art.

The medical device may further consist of at least one optional ingredient. Some examples of suitable optional ingredients include emulsifiers, viscosity enhancers, dyes, pigments, fragrances, pH modifiers, wetting agents, plasticizers, antioxidants, and the like. The optional ingredients may represent up to about 10% of the mesh and/or film by weight.

In some embodiments, the film may include at least one plasticizer, i.e., glycerol, PEG, etc. For instance, in some embodiments, the film may include collagen, and at least one of PEG and glycerol.

The films described herein may be formed by any suitable method known to those skilled in the art. In certain embodiments, a solution may be formed which includes the suitable polymeric material and any optional ingredients. The solution may be cast, bulk sheet stock, sprayed using an ultrasonic sprayer, extruded, molded and the like, to form the films described herein. Suitable solvents include, without limitation, methylene chloride, chloroform, N-methylpyrrolidone, tetrahydrofuran, dimethylformamide, methanol, ethanol, hexanes, acetone, water and combinations thereof.

In certain embodiments, the medical device and in particular, a film portion of the medical device may be created using a spraying technique, such as ultrasonic spraying. Spraying films may result in a unique ability to include a high therapeutic payload of a therapeutic agent. For example, the medical device as described herein may be fabricated by passing a first polymer solution and optionally a second solution containing a therapeutic agent through an ultrasonic spray nozzle to form droplets. The droplets may be mixed while falling towards or being deposited onto an inert substrate, such as silicone sheet, or a portion of a reinforcement member, such as a mesh, to form a film.

In some embodiments, the films include a single layer containing a polymer and a therapeutic agent. In other embodiments, the films include a first layer containing a polymer and a second layer containing a therapeutic agent. In still other embodiments, the films include a tri-layer structure wherein a second layer containing a therapeutic agent is positioned between a first layer containing a polymer and a third layer containing the same or different polymer.

Medical devices of the present disclosure may further comprise a therapeutic agent. The term "therapeutic agent", as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic effect, such as, anti-adhesives, antimicrobials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the films described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present foldable films include, lidocaine, bupivicaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenytoin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cycothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophosphamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof.

In some embodiments, the therapeutic agent may include an anesthetic, i.e., bupivicaine, lidocaine, benzocaine, and the like.

Although the above therapeutic agents have been provided for the purposes of illustration, it should be understood that the present disclosure is not so limited. In particular, although certain therapeutic agents are specifically referred to above, the present disclosure should be understood to include analogues, derivatives and conjugates of such agents.

The therapeutic agent may be combined with any portion of the medical device, including the film and/or the reinforcement member. In some embodiments, the therapeutic agent may be included in the foldable film to provide sustained release of the therapeutic agent following implantation.

The implantable medical devices described herein may also include at least one reinforcement member. Some non-limiting examples of suitable reinforcement members include staple fibers and surgical mesh. The surgical mesh described herein may include porous fabrics made from intertwined filaments. The filaments may extend horizontally and vertically in a manner which produces sections where the filaments cross-over one another creating points of common intersection. The surgical mesh may be woven, non-woven, knitted or braided. In some embodiments, the filaments may form two-dimensional or three-dimensional meshes. Some examples of two-dimensional and/or three-dimensional mesh substrates may be found in U.S. Pat. No. 7,021,086, U.S. Pat. No. 6,596,002, and U.S. Pat. No. 7,331,199, the entire contents of which are incorporated by reference herein.

Suitable meshes for use in the present disclosure include, for example, a collagen composite mesh such as PARIETEX™ Composite Mesh (commercially available from Tyco Healthcare Group LG, d/b/a Covidien). PARIETEX™ Composite Mesh is a 3-dimensional polyester weave with a resorbable collagen film bonded on one side. Another suitable mesh includes Parietex Progrip™ self-fixating mesh (also commercially available from Covidien). Parietex Progrip™ is a polyester mesh which includes poly lactic acid (PLA) grip members. Other suitable meshes include those sold under the names PARIETENE®, PARIETEX™, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); PROLITE®, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT® mesh (all commercially available from W.L. Gore). Additionally, meshes within the scope and context of this disclosure may include biologic materials such as allografts (i.e., AlloDerm® Regenerative Tissue Matrix from Lifecell), autografts, and xenografts (i.e., PERMACOL™, from Covidien). In alternate embodiments, processed/purified tissues may also be employed.

In certain preferred embodiments, Parietex™ Composite Mesh or Parietex™ Pro-grip may be utilized in accordance with the present invention.

The reinforcement members may be monofilaments or multi-filaments and, in embodiments, a plurality of multi-filaments may be combined to form yarns. It is envisioned that the reinforcement members may be configured to any suitable size and/or shape. The filaments may comprise core/sheath constructs.

In certain embodiments, the reinforcement member may be a surgical mesh knitted on a warp knitting machine, of the tricot or Raschel type, with at least three sheets or warps of yarn and as many guide bars.

Figure 7:
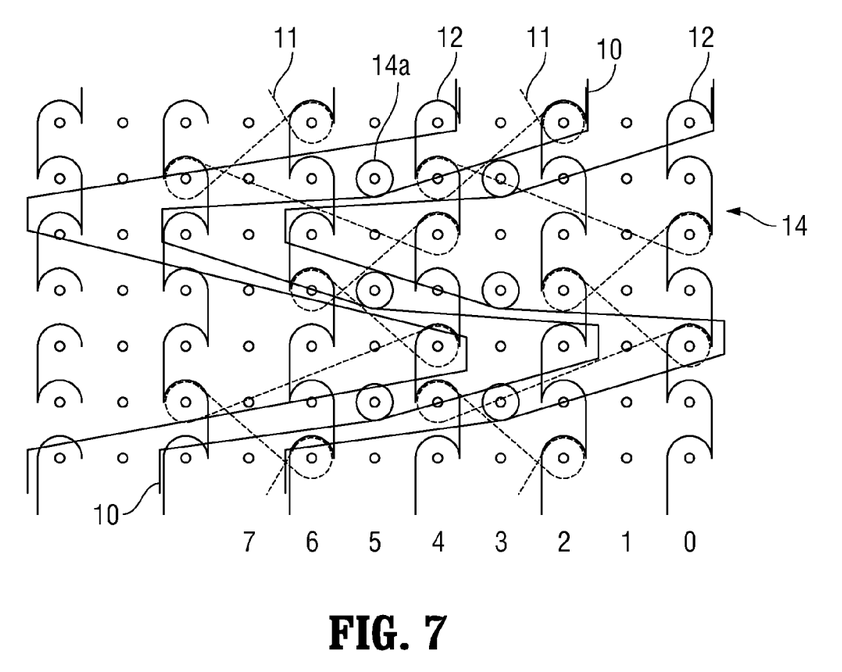
FIG. 7 is a diagram showing the weave of three sheets forming a reinforcement member according to at least one of the embodiments described in the present disclosure; and, FIG. 8 is a diagrammatic side view of a device permitting the formation of grip members on a reinforcement member according to at least one of the embodiments described in the present disclosure.

A rear bar may be threaded, one guide full and one guide empty, with first mono- or multi-filaments 10 of a biocompatible polymer as represented as a solid line in FIG. 7. An intermediate bar is threaded, one guide full, three guides empty, with second mono- or multi-filaments 11 of a biocompatible polymer as represented as a broken line in FIG. 7. The intermediate bar works in such a way as to obtain a zigzag openwork pattern between the columns of meshes. Finally, a front bar is threaded, one guide full, one guide empty, and works in a chain stitch with third mono- or multi-filaments 12 a biocompatible polymer as represented by a thin line in FIG. 7. The third filament 12, i.e., a chain stitch, imprisons first filament 10 and maintains the length of the mesh while contributing to the formation of the mesh with the intermediate sheet formed by the second filament 11. The different filaments may form yarns and may be worked according to the following chart:

| Warp | | |
|---|---|---|
| Rear bar I | Intermediate bar II Raschel | Front bar III |
| Front bar I | Intermediate bar II | Rear bar III |
| 7 | 3 | 1 |
| 7 | 2 | 0 |
| 3 | 4 | 0 |
| 4 | 5 | 1 |
| 0 | 1 | |
| 0 | 0 | |
| 4 | 2 | |
| 3 | 3 | |
| | 1 | |
| | 0 | |
| | 4 | |
| | 5 | |

The rear bar places the first filament or yarn in partial weft under the chain stitch and "thrown" onto the needle not forming a chain stitch. For this reason, at the next row, the needle not forming a chain stitch not being supplied permits escape of the filament which forms a loop 14a projecting from the front face of the mesh.

The threading—one guide full, three guides empty—in the intermediate bar, associated with the displacement, makes it possible to form a light ground texture, stable in width, and open-worked to permit good tissue integration.

The mesh 14 thus obtained may be provided with loops 14a (FIG. 8) which may be perpendicular to one of the mesh surfaces. Loops 14a may also include a rigidity and hold at a right angle which may be obtained by the rigidity or nerve of the filaments employed. This rigidity may be necessary for the subsequent formation of grip members which ensure a grip function to at least a portion of the implantable medical device.

Figure 8:
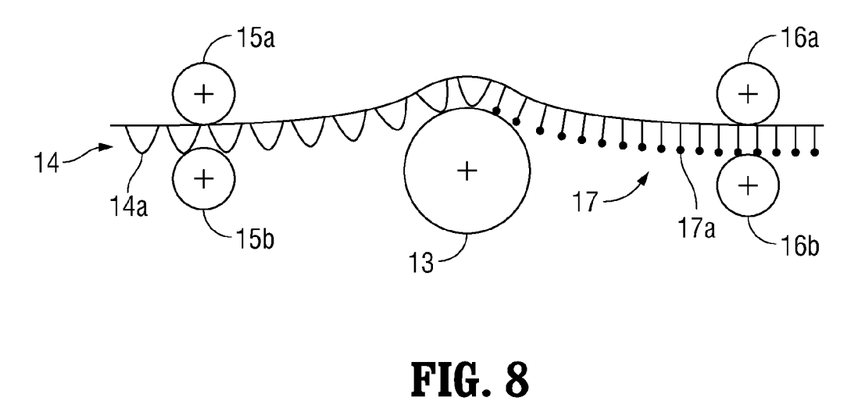

On leaving the loom, mesh 14 may be subjected to a thermosetting operation which stabilizes the mesh length and width. The mesh may then be subjected to a phase of formation of the grip members consisting, as is shown in FIG. 8, in passing the mesh over a cylinder 13 containing an electrical heating resistor. Mesh 14 is pressed flat on cylinder 13 by two pairs of rollers, upstream 15a, 15b and downstream 16a, 16b, respectively, which are vertically displaceable for controlling this pressing force.

This control as well as that of the temperature of the resistor placed in cylinder 13 and of the speed of movement of mesh 14 across cylinder 13 make it possible to melt the head of each of loops 14a so that each loop 14a forms two grip members 17

Each grip member 17 thus may have a substantially rectilinear body protruding perpendicularly with respect to mesh 14 and, at the free end of this body, a head 17a of greater width than that of the body. Head 17a has a generally spheroidal shape or a mushroom shape. Grip member 17 gives mesh 14 the ability to attach to tissue when implanted. In addition, grip members 17 may attach to other portions of mesh 14 when folded or rolled. The grip members may be positioned along any portion of the mesh and in any quantity and/or configuration. For example, in some embodiments, the grip members may be positioned on the same portion of the mesh as the film. In other embodiments, the grip members may be positioned on a different portion of the mesh which does not include the film.

Any biocompatible material may be used to form the reinforcement members described herein. For example, the reinforcement members may be made from non-bioabsorbable materials, bioabsorbable materials and combinations thereof. Suitable materials are within the purview of those skilled in the art.

The reinforcement member and the foldable film may be combined using any suitable method known to those skilled in the art. For example, the reinforcement member may be staple fibers which are combined in a mold with the polymeric film material prior to forming the foldable films.

In some embodiments, the reinforcement member is a mesh material and the foldable film may be cast directly on a portion of the mesh surface. In other embodiments, the film may be spray coated directly on a portion of the mesh. It is envisioned that the thicker areas of the foldable film may be sprayed for a longer duration of time and/or at a higher volume than the thinner areas of the foldable film. In still other embodiments, the film may be formed before being connected to the mesh. In additional embodiments, the foldable film may be positioned within a mold which creates the thicker and thinner portions of the foldable film described herein. Prior to the complete formation of the film, the reinforcement member may be placed in contact with the gelling film material. In some instances the reinforcement member may be completely embedded in the film. In other instances, only a portion of the reinforcement member may be in contact with the foldable film. For example, the outer surface of the reinforcement member, i.e., a mesh, may be placed on top of the gelling film layer without the gelling film layer penetrating into the pores of the mesh.

Figure 1A:
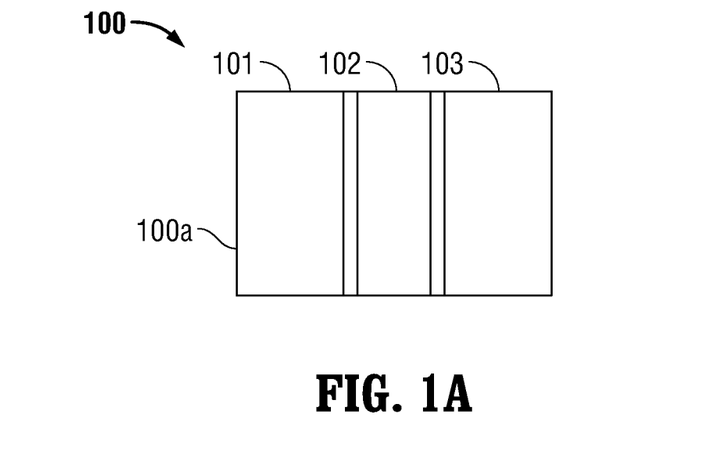
FIG. 1A is a top view of an implantable medical device according to at least one embodiment described in the present disclosure.
Figure 1B:
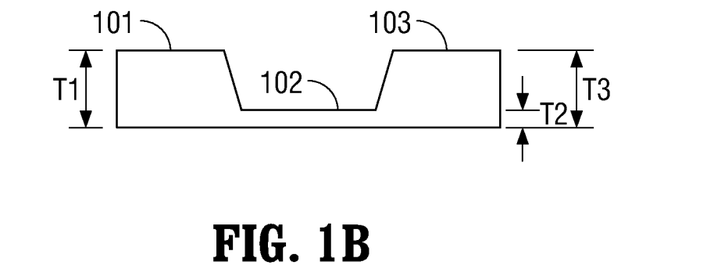
FIGS. 1B and 1C are a side view of an implantable medical device according to the embodiment shown in FIG. 1A.
Figure 1C:
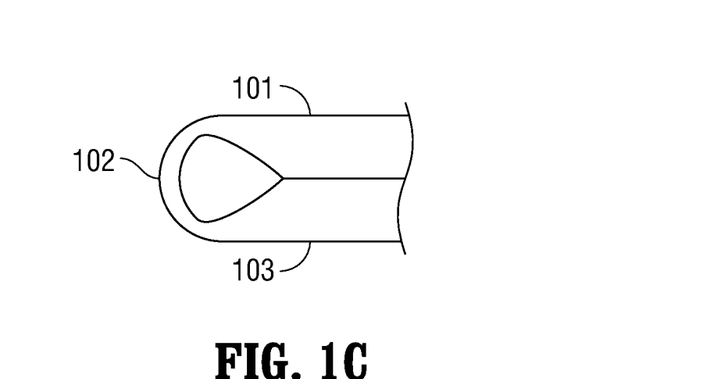

Turning now to FIGS. 1A-1C, implantable medical device is illustrated including foldable film 110 including first area 101 having first thickness T1, second area 102 having second thickness T2, and third area 103 having third thickness T3, wherein second area 102 is positioned between first area 101 and third area 103 of the film 110. Second thickness T2 of second area 102 is less than first thickness T1 and third thickness T3. Although depicted as being generally the same, the first and third thicknesses may be the same or different, as needed to provide the implant with folding characteristics.

In the folded configuration, first area 101 and third area 103 may be placed adjacent to each other with second area 102 extending between first area 101 and third area 103. It is envisioned that since second area 102 is thinner than first and third areas 101, 103, second area 102 may bend or flex to allow the first and third areas 101, 103 to be folded on top of one another (FIG. 1C). However, in some embodiments, second area 102 may be made from a different material than first and third areas 101, 103 which is more flexible than the materials of first and third areas 101, 103.

Figure 2A:
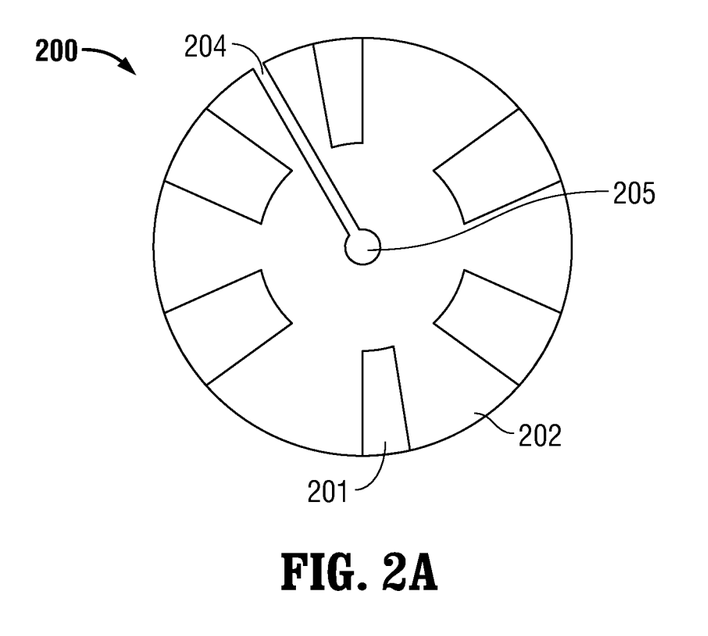
FIG. 2A is a top view of an implantable medical device according to at least one embodiment described in the present disclosure.
Figure 2B:
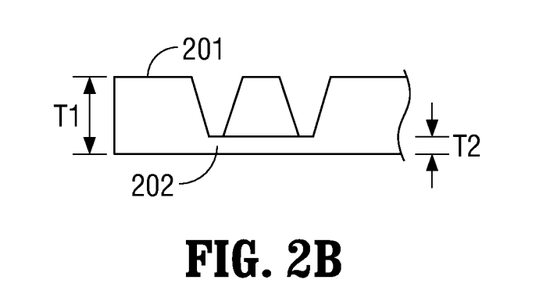
FIGS. 2B and 2C are a side view of an implantable medical device according to the embodiment shown in FIG. 2A.
Figure 2C:
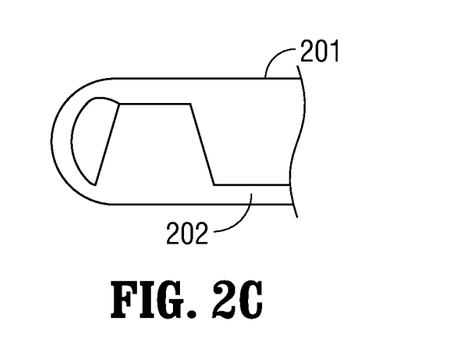

In FIGS. 2A-2C, implantable medical device is illustrated including foldable film 200 including first area 201 having first thickness T1' and second area 202 having second thickness T2' wherein first and second areas 201, 202 extend around outer edge 207 of film 200a in an alternating manner. Film 200a further include aperture 205 which as shown may be generally centrally located, and slit 204 which extends between a portion of outer edge 207 and aperture 205 to allow tissues, organs, implants and the like to be positioned therein. As shown, first areas 201 and second areas 202 are not positioned around film 200 in a symmetrical pattern. As shown in FIG. 2C, folded film 200 positions first area 201 adjacent second area 202. Thus, in some embodiments, the overall thickness of the folded film is equal to the sum of the first thickness of the first area and the second thickness of the second area. It is envisioned that the dimensions of the first and second areas may be configured to create a snug fit between the first areas and the second areas when the film is folded, thereby temporarily locking the film in a folded configuration.

Figure 5A:
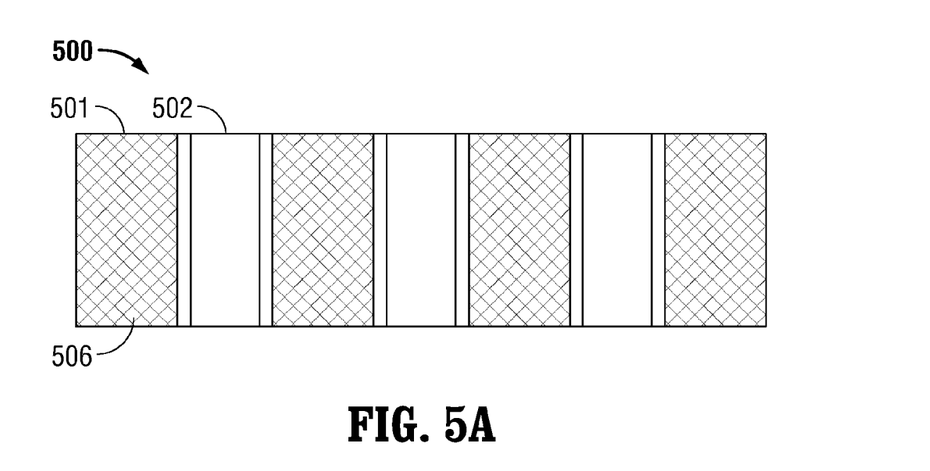
FIG. 5A is a top view of an implantable medical device according to at least one embodiment described in the present disclosure.
Figure 5B:
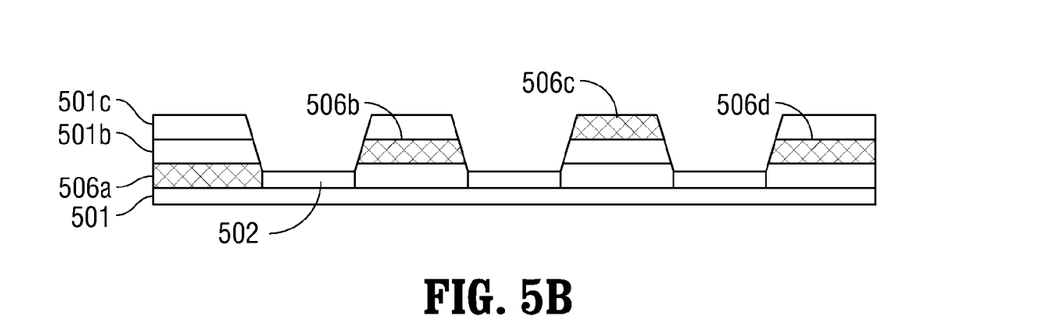
FIGS. 5B and 5C are a side view of an implantable medical device according to the embodiment shown in FIG. 5A.

In some embodiments, the alternating pattern of first and second areas may be symmetrical so when folded the first areas are positioned adjacent to additional first areas (FIG. 5B)

Figure 3A:
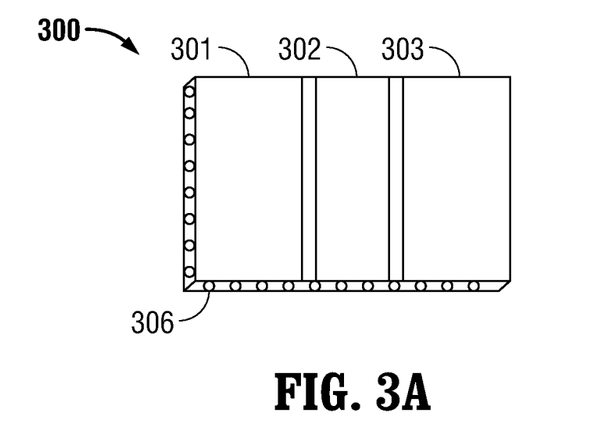
FIG. 3A is a perspective view of an implantable medical device according to at least one embodiment described in the present disclosure.
Figure 3B:
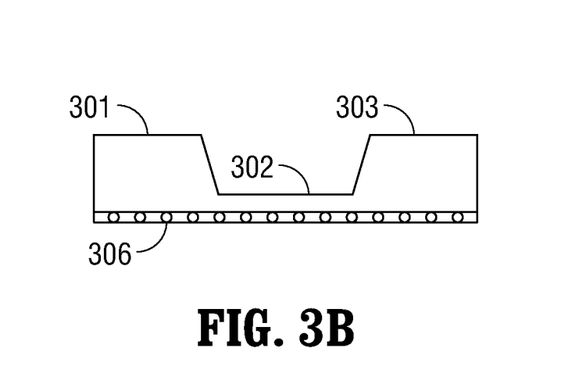
FIGS. 3B and 3C are a side view of an implantable medical device according to the embodiment shown in FIG. 3A.
Figure 3C:
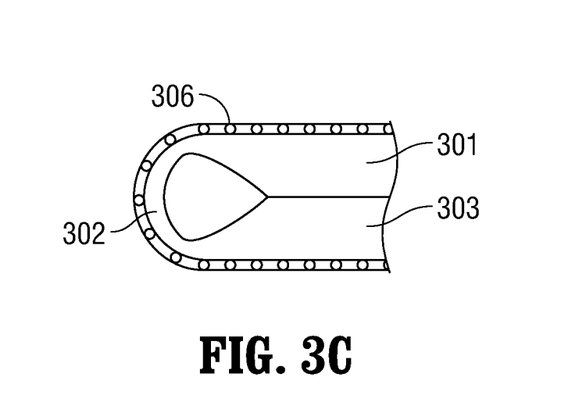

In FIGS. 3A-3C, implantable medical device includes foldable film 300 and at least one reinforcement member 306. Reinforcement member 306 is shown as a surgical mesh or textile attached to first, second and third areas 301, 302, 303 of film 300a. In some embodiments, the mesh may be stiffer than at least a portion of the film and may provide tension to the film to return to a generally planar configuration (FIGS. 3A-3B) from the folded configuration (FIG. 3C).

Figure 4A:
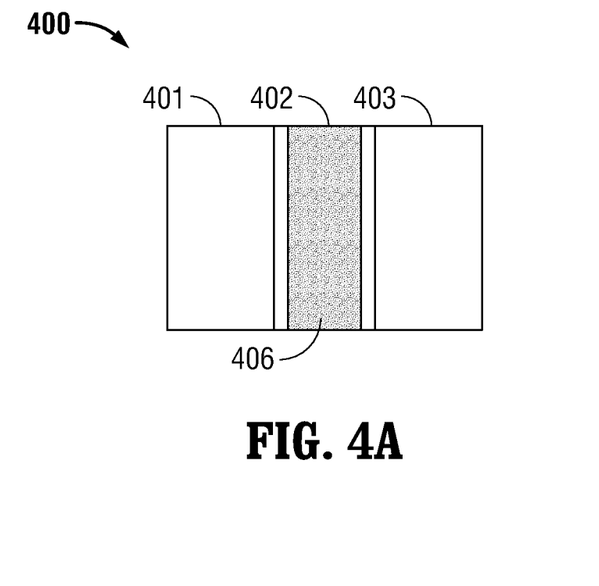
FIG. 4A is a top view of an implantable medical device according to at least one embodiment described in the present disclosure.
Figure 4B:
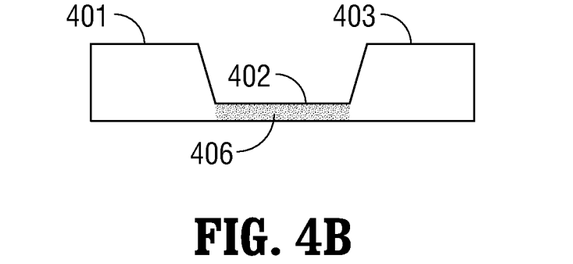
FIGS. 4B and 4C are a side view of an implantable medical device according to the embodiment shown in FIG. 4A.
Figure 4C:
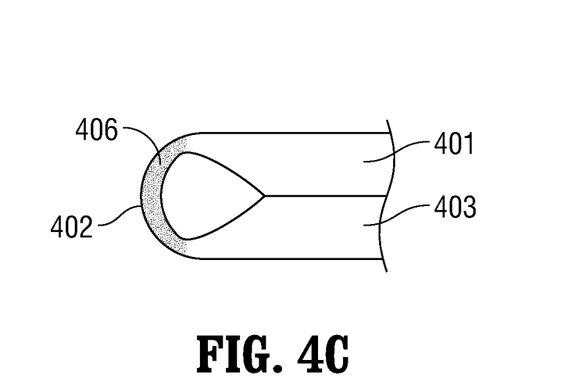

As illustrated in FIGS. 4A-4C, in some embodiments, reinforcement member 406 may be positioned within second area 402 of foldable film 400. In some embodiments, the addition of reinforcement members 406 may enhance the structural integrity of second area 402 to withstand the repeated folding and unfolding of the implant.

Figure 5C:
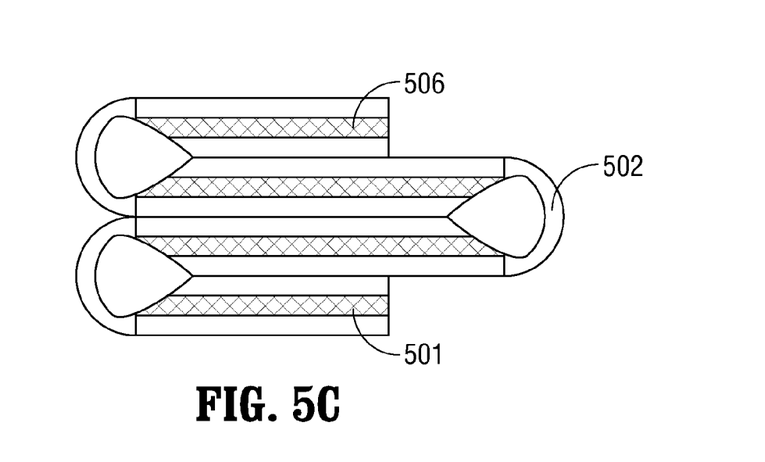

In other embodiments, such as those shown in FIGS. 5A-5C, implantable medical device includes multilaminar foldable film 500 which includes reinforcement member 506 positioned within at least one of the multiple layers 501a-501c of first area 501 which is thicker than second area 502.

As shown, reinforcement members 506a-d may be positioned within different layers 501a-c in each of the different first areas 501.

Figure 6A:
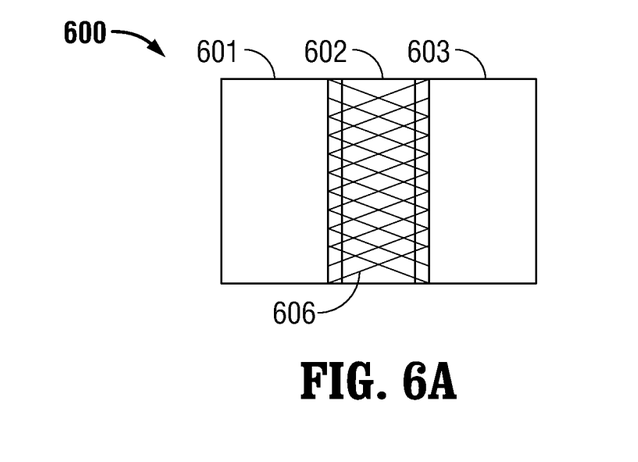
FIG. 6A is a top view of an implantable medical device according to at least one embodiment described in the present disclosure.
Figure 6B:
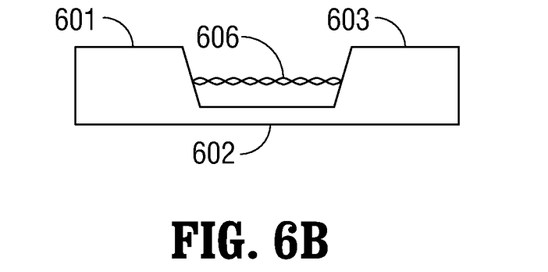
FIGS. 6B and 6C are a side view of an implantable medical device according to the embodiment shown in FIG. 6A.
Figure 6C:
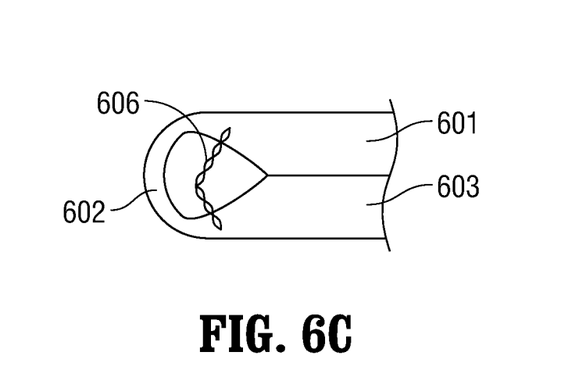

In still other embodiments, such as those depicted in FIGS. 6A-6C, implantable medical device includes foldable film 600 which includes reinforcement member 606 extending between first area 601 and third area 603 and spanning second area 602. As shown in FIG. 6C, reinforcement member 606, i.e., surgical mesh, may be positioned between first, second and third areas 601, 602, 603 in the folded configuration. In some embodiments, the mesh may be stiffer than at least a portion of the film and may provide tension to the film to return the film to its original generally planar configuration (FIGS. 6A-6B) from the folded configuration (FIG. 6C).

Although shown in a generally planar configuration, the implantable medical devices described herein may not be limited to planar configurations only and may represent non-planar configurations as well. In embodiments, the reinforcement member may assist the implant to return to its original non-planar configuration.

Although shown previously as generally circular, square and/or rectangular in shape, the implants described herein including the film and/or the reinforcement member may be of any shape.

The implants described herein may be useful in many endoscopic, laparoscopic, arthroscopic, endoluminal, transluminal, and/or open surgical procedures. Some examples include hernia repair, repair of vaginal prolapse, ligament repair, tendon repair, and the like. Although the polymeric films described herein may be made from any biocompatible materials, in certain procedures, the film layers may be made from anti-adhesive materials. For example, when implanting the medical devices described herein into tissue near Cooper's ligament, it might be useful to have the flexibility to wrap around or surround the ligament, or any other sensitive tissue such as the spermatic cord, tendons, intestinal tissue, etc.

It will be understood that various modifications may be made to the embodiments disclosed herein. For example, the medical devices described herein may be sterilized and packaged into using any suitable sterilization process, i.e., gamma radiation, and any suitable medical device package, i.e., an injectable medical device package. In other examples, the implants described herein may include more than one film, reinforcement member, aperture, slot, and/or therapeutic agent. Thus, those skilled in the art will envision other modifications within the scope and spirit of the claims.

What is claimed is:

1. An implantable medical device comprising:
    a foldable anti-adhesive film having a discontinuous planar top surface and a bottom planar surface, the foldable film including a first area having a first thickness defined by a first top surface and the bottom planar surface, a second area having a second thickness defined by a second top surface and the bottom planar surface, and a third area having a third thickness defined by a third top surface and the bottom planar surface, wherein the second area is positioned between the first and third areas along the bottom planar surface of the film and the second thickness of the second area is less than the first thickness and the third thickness; and
    a reinforcement member attached to and in direct contact with the bottom planar surface of the foldable film, wherein the reinforcement member is a porous surgical mesh which permits tissue integration.

2. The implantable medical device of claim 1 wherein the first thickness and the third thickness are the same.

3. The implantable medical device of claim 1 wherein the foldable film comprises a multilaminar film.

4. The implantable medical device of claim 1 wherein the reinforcement member is attached to the bottom planar surface of the first area of the film.

5. The implantable medical device of claim 1 wherein the reinforcement member is attached to the bottom planar surface of the second area of the film.

6. The implantable medical device of claim 1 wherein the reinforcement member is attached to the bottom planar surface of the third area of the film.

7. The implantable medical device of claim 1 wherein the reinforcement member is attached to the bottom planar surface of the first, second, and third areas of the film.

8. The implantable medical device of claim 1 wherein an outer surface of the reinforcement member is attached to the bottom planar surface of the film without the film penetrating into pores of the porous surgical mesh.

9. An implantable medical device comprising:
a foldable anti-adhesive film having a discontinuous planar top surface and a bottom planar surface, the foldable film including a first area having a first thickness defined by a first top surface and bottom planar surface of the film, and a second area having a second thickness defined by a second top surface and bottom planar surface of the film, wherein the second thickness is less than the first thickness of the first area, and the first and second areas alternate along the bottom planar surface of the device; and
a reinforcement member attached to and in direct contact with the bottom planar surface of the foldable film, wherein the reinforcement member is a porous surgical mesh which permits tissue integration.

10. The implantable medical device of claim 9 wherein the first thickness and the second thickness are at a ratio ranging from about 2:1 to about 20:1.

11. The implantable medical device of claim 9 wherein the foldable film comprises a multilaminar film.

12. The implantable medical device of claim 11 wherein the reinforcement member is attached to the bottom planar surface of the first area of the multilaminar film.

13. The implantable medical device of claim 9 wherein the porous surgical mesh further comprises at least one grip member.

14. The implantable medical device of claim 9 wherein the foldable film further comprises at least one therapeutic agent.

15. An implantable medical device comprising:
a foldable anti-adhesive film having a discontinuous planar top surface and a bottom planar surface, the foldable film including a first area having a first thickness defined by a first top surface and bottom planar surface, a second area having a second thickness defined by a second top surface and bottom planar surface, and a third area having a third thickness defined by a third top surface and bottom planar surface, wherein the second area is positioned between the first and third areas along the bottom planar surface of the film and the second thickness of the second area is less than at least one of the first thickness and the third thickness, and,
a reinforcement member attached to and in direct contact with the bottom planar surface of the foldable film, wherein the reinforcement member is a porous surgical mesh which permits tissue integration.

16. The implantable medical device of claim 15 wherein the reinforcement member is attached to the bottom planar surface of the first, second, and third areas of the film.

17. The implantable medical device of claim 15 wherein an outer surface of the reinforcement member is attached to the bottom planar surface of the film without the film penetrating into pores of the porous surgical mesh.

18. The implantable medical device of claim 9 wherein the reinforcement member is attached to the bottom planar surface of the first and second areas of the film.

19. The implantable medical device of claim 9 wherein an outer surface of the reinforcement member is attached to the bottom planar surface of the film without the film penetrating into pores of the porous surgical mesh.

* * * * *